United States Patent
Kumar et al.

(10) Patent No.: US 10,137,094 B2
(45) Date of Patent: Nov. 27, 2018

(54) GASTRORETENTIVE DOSAGE SYSTEM AND PROCESS OF PREPARATION THEREOF

(71) Applicant: RANBAXY LABORATORIES LIMITED, New Delhi, Delhi (IN)

(72) Inventors: Varinder Kumar, Sangrur (IN); Shavej Ahmad, Lucknow (IN); Romi Barat Singh, Varanasi (IN)

(73) Assignee: Sun Pharmaceutical Industries Limited, Mumbai (IN)

(*) Notice: Subject to any disclaimer, the term of this patent is extended or adjusted under 35 U.S.C. 154(b) by 0 days.

(21) Appl. No.: 14/350,615

(22) PCT Filed: Oct. 11, 2012

(86) PCT No.: PCT/IB2012/055514
§ 371 (c)(1),
(2) Date: Apr. 9, 2014

(87) PCT Pub. No.: WO2013/054285
PCT Pub. Date: Apr. 18, 2013

(65) Prior Publication Data
US 2014/0271846 A1  Sep. 18, 2014

(30) Foreign Application Priority Data
Oct. 11, 2011 (IN) .......................... 2922/DEL/2011

(51) Int. Cl.
| | |
|---|---|
| *A61K 9/48* | (2006.01) |
| *A61K 9/00* | (2006.01) |
| *A61K 31/197* | (2006.01) |
| *A61K 31/495* | (2006.01) |

(52) U.S. Cl.
CPC .......... *A61K 9/4833* (2013.01); *A61K 9/0065* (2013.01); *A61K 9/4808* (2013.01); *A61K 9/4891* (2013.01); *A61K 31/197* (2013.01); *A61K 31/495* (2013.01)

(58) Field of Classification Search
CPC .. A61K 31/495; A61K 31/197; A61K 9/4891; A61K 9/4833
See application file for complete search history.

(56) References Cited

U.S. PATENT DOCUMENTS

| | | | |
|---|---|---|---|
| 3,976,764 A | 8/1976 | Watanabe et al. | 424/19 |
| 4,973,480 A * | 11/1990 | Hermelin | A61K 9/4891 424/453 |
| 5,300,300 A | 4/1994 | Egidio et al. | 424/456 |
| 5,626,876 A | 5/1997 | Müller et al. | 424/484 |
| 6,207,197 B1 | 3/2001 | Illum et al. | 424/491 |
| 7,485,322 B2 | 2/2009 | Kerc | 424/453 |
| 7,604,820 B1 | 10/2009 | Shimono et al. | 424/468 |
| 2005/0064027 A1 | 3/2005 | Jacob et al. | 424/451 |
| 2008/0020041 A1* | 1/2008 | Ayres | A61K 9/5078 424/472 |
| 2008/0107732 A1* | 5/2008 | Dharmadhikari et al. | 424/482 |

FOREIGN PATENT DOCUMENTS

WO  WO 2005/101983  11/2005  ............... A61K 9/28

OTHER PUBLICATIONS http://eudragit.evonik.com/product/eudragit/en/products-services/eudragit-products/enteric-formulations/I-100-55/pages/default.aspx as referenced on Jan. 28, 2015.*
http://www.drugs.com/pro/baclofen.html as referenced on Jan. 29, 2015.*
Jackson et al., "Comparative scintigraphic assessment of the intragastric distribution and residence of cholestyramine, Carbopol 934P and sucralfate", *International Journal of Pharmaceutics*, 212(1):55-62 (2001).
Hampson et al.,"Alginate rafts and their characterisation", *International Journal of Pharmaceutics*, 294(1-2):137-147 (2005).
Chavanpatil et al., "Development of sustained release gastroretentive drug delivery system for ofloxacin: In vitro and in vivo evaluation", *International Journal of Pharmaceutics*, 304(1-2):178-184 (2005).
Arora et al., "Floating Drug Delivery Systems: A Review", *AAPS PharmSciTech*, 6(3):E372-E390 (2005).

* cited by examiner

*Primary Examiner* — Jessica Worsham

(57) ABSTRACT

The present invention relates to novel gastroretentive dosage systems, in particular, a floating capsule which releases the drug without any lag time and which remains buoyant for a sufficient period of time in the stomach. Further, the invention relates to the process of preparation thereof.

6 Claims, No Drawings

GASTRORETENTIVE DOSAGE SYSTEM AND PROCESS OF PREPARATION THEREOF

FIELD OF THE INVENTION

The present invention relates to gastroretentive dosage systems, in particular, a floating capsule which releases the drug without any lag time and which remains buoyant for a sufficient period of time in the stomach. Further, the invention relates to the process of preparation thereof.

BACKGROUND OF THE INVENTION

Due to the ease of administration, patient compliance, and variability in formulations, the oral route of administration remains the most preferred route of administration. Amongst oral, a site specific drug delivery system remains the system of choice in many circumstances. This system can also help in optimizing oral-controlled delivery of drugs having an "absorption window" by continuously releasing the drug prior to the absorption window, for a prolonged period of time thus causing optimal bioavailability. Gastric emptying of dosage forms is an extremely variable process and the ability to prolong and control the emptying time is a valuable asset for dosage forms, which reside in the stomach for a longer period of time than conventional dosage forms. Prolonged gastric residence time and controlled-release of drugs within the gastrointestinal tract helps to reduce the dosing frequency and total dose, improve patient compliance and convenience, and maintain a less fluctuating plasma level, as well as reduce GI side effects. Prolonging of the gastric residence time of the therapeutic agents is thought to be beneficial, especially under several circumstances such as for drugs acting topically on the gastric region, for drugs with a narrow therapeutic window, for drugs with the major absorption site in the upper GI tract and for drugs that are less soluble in or are degraded by the alkaline pH of the upper GI tract.

The prior art discloses different approaches or systems to prolong the gastric residence time, such as mucoadhesive or bioadhesive systems, high density systems, expandable or swelling systems, and floating drug delivery systems.

The mucoadhesive systems are intended to extend the gastric residence time by adhering the drug to the gastric mucous membrane. Bioadhesion on soft tissues of certain natural or synthetic polymers has been exploited to control as well as to prolong the gastric retention of the delivery system. Jackson et al., in "Comparative Scintigraphic Assessment of the Intragastric Distribution and Residence of Cholestyramine, Carbopol 934P and sucralfate", *Int. J. Pharm.*, 212(1):55-62(2001); U.S. Pat. No. 6,207,197; and U.S. Patent Application No. 2005/0064027 describe the mucoadhesive gastroretentive system.

High density systems are intended to lodge in the rugae or folds of the stomach withstanding the peristaltic movements. Systems with a density of 1.3 g/ml or higher are expected to be retained in the lower part of the stomach. Hampson et al., "Alginate Rafts and Their Characterization", *Int. J. Pharm.*, 294(1-2):137-147 (2005) describe the high density gastroretentive systems.

Expandable or swelling systems are easily swallowed and reach a significantly larger size in the stomach due to swelling or unfolding processes that prolong their time in the gastrointestinal tract. After drug-release, their dimensions are minimized with subsequent evacuation from the stomach. Chavanpatil et al., "Development of Sustained Release Gastroretentive Drug Delivery System for Ofloxacin: In vitro and in vivo Evaluation", *Int. J. Pharm.*, 304(1-2):178-184 (2005) describe the swelling gastroretentive system.

Floating drug delivery systems have a bulk density less than gastric fluids and so remain buoyant in the stomach without affecting gastric emptying rate for a prolonged period of time. While the system is floating on the gastric contents, the drug is released slowly at the desired rate from the system. After release of the drug, the residual system is emptied from the stomach. Arora et al., "Floating Drug Delivery Systems: A review", *AAPS PharmSciTech* 6(3): E372-E390 (2005) describes the floating gatroretentive system. The floating drug system can further be classified into effervescent systems such as gas generating systems and non-effervervescent systems such as colloidal gel barrier systems, microporous compartment system, floating microspheres and alginate floating beads.

GLUMETZA® GR (metformin hydrochloride), CYTOTEC® (misoprostol), CONVIRON® (vitamin B12—combination), CIFRAN® OD (ciprofloxacin), MADOPAR® (levodopa and benserazide), and VALRELEASE® (diazepam) are some of the marketed preparations based on gastroretentive dosage forms.

U.S. Pat. No. 3,976,764 discloses solid therapeutic preparations floatable in the gastric juice wherein the active ingredient is impregnated into a body of empty globular shell or a small granular lump of a material having high buoyancy. The empty shells of the invention are gelatin capsules coated with active ingredients. The invention also discloses pop-corn or pop-rice type of materials coated with active ingredients.

Aerogels and foam materials have been used to produce floating systems. Due to entrapped air and gases in their hollow spaces, they are inherently less dense and hence float on the gastric fluids. U.S. Pat. No. 5,626,876 discloses floatable oral therapeutic systems which use microporous materials having a high void proportion for obtaining low specific gravity. The materials used are thermoplastic polymers, natural polymers and inorganic compounds such as glasses and ceramic materials. The invention relates to the preparation of microporous materials by processes such as granulation, hot melting, compression or molding. However, use of microporous materials tends to increase the bulk of the systems. There is also less flexibility for designing the dosage form and incorporating active ingredients. Such systems may also be complex and less reproducible.

U.S. Pat. No. 7,485,322 discloses a floating capsule dosage form having prolonged gastric residence time, wherein the capsule body and cap are assembled such as to encapsulate at least a tablet and granulate together with entrapped gas and is coated with a coating which is substantially insoluble or poorly soluble in an acidic medium. In this reference, the tablet and granulate comprise active and hydrophilic or lipophilic substances which helps in controlling the release. The active-release is controlled by a dual mechanism, one with the help of hydrophilic or lipophilic substances in the matrix of tablet and granulates, and second with the help of an outer coating layer. This increases the processing steps and also the complexity of the dosage form, as it would be critical to control the amount of hydrophilic and lipophilic substances in the granulate and/or tablet and to control the thickness of the coating. Further, a large amount of excipients would be required resulting in high cost. The main disadvantage with this system in particular, and with other known gastroretentive dosage systems, is that these systems release the drug after some time and there always remains the initial lag time. This may not be acceptable in instances where immediate drug-release would be required.

There is a need in the art to formulate a gastroretentive dosage system which is simple, safe, cost-effective, easy to manufacture and is functionally reproducible.

We have now developed a gastroretentive dosage system which controls the release of the active ingredient only with the help of coating, making it simple and cost-effective. Further, the gastroretentive dosage system is designed to start releasing the active ingredient without any lag time. The gastroretentive dosage system can incorporate high amount of active ingredient and therefore this system can be explored for high dose active ingredients. Further, the system can be used for pulsatile drug delivery and combination of active ingredients in particular, incompatible active ingredients.

SUMMARY OF THE INVENTION

In one of the general aspects, there is provided a gastroretentive dosage system comprising:
(a) a shell filled with the active ingredient in powder form; and
(b) an extended-release layer over the shell.

In another general aspect there is provided a gastroretentive dosage system comprising:
(a) a shell filled with the active ingredient and one or more pharmaceutically acceptable excipient(s) in powder form; and
(b) an extended-release layer over the shell.

In another general aspect, there is provided a gastroretentive dosage system comprising:
(a) a shell filled with the active ingredient in powder form;
(b) an extended-release layer over the shell; and
(c) an immediate-release layer comprising the active ingredient over the extended-release layer.

In another general aspect, there is provided a gastroretentive dosage system comprising:
(a) a shell filled with the active ingredient and one or more pharmaceutically acceptable excipient(s) in powder form;
(b) an extended-release layer over the shell; and
(c) an immediate-release layer comprising the active ingredient over the extended-release layer.

In another general aspect, there is provided a gastroretentive dosage system comprising:
(a) a shell filled with the active ingredient in powder form;
(b) an extended-release layer comprising one or more extended-release polymer(s), one or more coating additive(s); and
(c) an immediate-release layer comprising the active ingredient, one or more binder(s) and one or more coating additive(s).

In another general aspect, there is provided a gastroretentive dosage system comprising:
(a) a shell filled with the active ingredient and one or more pharmaceutically acceptable excipient(s) in powder form;
(b) an extended-release layer comprising one or more extended-release polymer(s), one or more coating additive(s); and
(c) an immediate-release layer comprising the active ingredient, one or more binder(s) and one or more coating additive(s).

In another general aspect, there is provided a gastroretentive dosage system comprising:

(a) a shell comprising the active ingredient, one or more osmotic agent(s), and one or more pharmaceutically acceptable excipient(s) in powder form;
(b) a semi-permeable layer comprising one or more semi-permeable membrane forming polymer(s), one or more flux enhancer(s), and one or more coating additive(s);
(c) an immediate-release layer comprising the active ingredient, one or more binder(s), one or more coating additive(s); and
(d) optionally at least one passageway.

In one of the embodiments, the active ingredient present in the shell and the active ingredient present in the immediate-release layer are similar.

In another embodiment, the active ingredient present in the shell and the active ingredient present in the immediate-release layer are different.

In another general aspect there is provided a process for the preparation of gastroretentive dosage system, wherein the process comprises the steps of:
(a) filling the empty shell with the active ingredient in powder form; and
(b) coating the shell with a solution or dispersion of one or more extended-release polymer(s) and one or more coating additive(s).

In another general aspect, there is provided a process for the preparation of a gastroretentive dosage system, wherein the process comprises the steps of:
(a) filling the empty shell with the blend of the active ingredient and one or more pharmaceutically acceptable excipient(s) in powder form; and
(b) coating the shell with a solution or dispersion of one or more extended-release polymer(s) and one or more coating additive(s).

In another general aspect, there is provided a process for the preparation of a gastroretentive dosage system, wherein the process comprises the steps of:
(a) filling the empty shell with the active ingredient in powder form;
(b) coating the shell with a solution or dispersion of one or more extended-release polymer(s) and one or more coating additive(s); and
(c) coating the above coated shells with a solution or dispersion of the active ingredient, one or more binder(s) and one or more coating additive(s).

In another general aspect, there is provided a process for the preparation of a gastroretentive dosage system, wherein the process comprises the steps of:
(a) filling the empty shell with the blend of the active ingredient and one or more pharmaceutically acceptable excipient(s) in powder form;
(b) coating the shell with a solution or dispersion of one or more extended-release polymer(s) and one or more coating additive(s); and
(c) coating the above-coated shells with a solution or dispersion of the active ingredient, one or more binder(s) and one or more coating additive(s).

In another general aspect, there may be provided a process for the preparation of a gastroretentive dosage system, wherein the process comprises the steps of:
(a) filling the empty shell with the active ingredient, one or more osmotic agent(s), and one or more pharmaceutically acceptable excipient(s) in powder form;
(b) coating the shell with a solution or dispersion of one or more semi-permeable membrane forming polymer(s), one or more flux enhancer(s) and one or more coating additive(s);

(c) coating the above coated shells with a solution or dispersion of the active ingredient, one or more binder(s), and one or more coating additive(s); and (d) optionally creating at least one passageway in the semi-permeable layer.

DETAILED DESCRIPTION OF THE INVENTION

In the gastroretentive dosage system of the present invention, first the outermost immediate-release layer comprising the active ingredient dissolves and releases the active ingredient in the stomach. After that, the extended-release coating, due to insolubility or poor solubility in an aqueous medium, prevents an influx of water into the shell for a predetermined period of time and air entrapped in the shell helps in floating the shell. In some of the aspects, the shell is filled with one or more osmotic agent(s) in addition to the active ingredient that swells with the help of water, creating an osmotic pressure that helps in complete and pH-independent release of the active ingredient. After the immediate burst release, the release is only controlled by the composition and thickness of a coating. Once the release process is initiated, the shell may still float or remain buoyant for a certain period of time in the medium or it may sink and disintegrate. The gastroretentive dosage system of the present invention remains floating for more than 1 hour, in particular for more than 12 hours.

The term "shell", as used herein, refers to hard or soft gelatin capsules, wafers or any aerogels or foam materials which are hollow and have a cavity inside which can entrap air. These shells may be precoated with a dispersion (solution or suspension) of a hydrophilic polymer, e.g., hydroxypropylmethylcellulose, hydroxypropylcellulose, or hydroxyethylcellulose. This precoating may protect the shell from being degraded by gastric juice, which can affect the floating performance in the stomach. It may also avoid rupture of the shell or change of shape of the shell in the stomach for a longer period of time.

In another embodiment, the shell comprises solely the active ingredient in the form of a powder.

In another embodiment, the shell comprises the active ingredient and one or more pharmaceutically acceptable excipient(s) in powder form.

In yet another embodiment, the shell comprises the active ingredient, one or more osmotic agent(s), and one or more pharmaceutically acceptable excipient(s) in powder form.

The term "active ingredient", as used herein, includes, but is not limited to drugs which are mainly absorbed in the stomach, drugs having higher solubility in the stomach than in the intestine, drugs which are poorly absorbed or degraded in the intestine, drugs requiring local effect in the stomach, etc. Specific examples include, but are not limited to, active nucleic acids or amino acids and their derivatives, peptidomimetic substances, antiulcer agents, some analgesics, antipsychotics, antidepressants, antiepileptics, cytostatics, antimigraine agents, antiviral substances, antibiotics, anti-inflammatory agents, sedatives, antidiabetic agents, antihistamines, therapeutic ions, vitamins, bronchodilators, antihypertensives, diuretics, hypolipemic agents, and anti-obesity agents.

Specific examples of active ingredients include, but are not limited to, acyclovir, gabapentin, pregabalin, trimetazidine, feropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifentidine, roxatidine, omeprazole, lansoprazole, pantoprazole, antacids such as magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, furosemide, topiramide, hydrochlorothiazide, orlistat, and pharmaceutically acceptable salts, esters or prodrugs thereof. The dose of any active ingredient would depend on the individual active substance. The invention particularly can be used for active ingredients where the dose is high, e.g., more than 500 mg.

The active ingredient present in the shell and the active ingredient present in the immediate layer of the dosage form are either similar or different. The active ingredients may belong to a similar therapeutic class or to a different therapeutic class. The active ingredients may be incompatible or a combination of high and low-dose active ingredients.

When both the shell and immediate-release layers comprise similar active ingredients, pulsatile-release can be achieved. First, there is a burst of immediate-release from the outer active layer, and after a predetermined time interval there is release of the active ingredient from the shell resulting in a pulsatile delivery. Also the system may provide the initial burst-release which provides the appropriate active concentration at the initial stage, followed by a constant drug-release without any lag, thereby maintaining the stable plasma concentration.

Extended-release polymers used in the present invention include polymers which are insoluble in an aqueous medium or a combination of polymers which are insoluble in an aqueous medium with water-soluble polymers. The amount of extended-release polymer used may vary from about 1% to about 20% w/w based on the total dosage form.

Specific examples of extended-release polymers which are insoluble in an aqueous medium include, but are not limited to, cellulose acetate phthalate, cellulose acetate mellitate, cellulose acetate succinate, cellulose acetate, hydroxypropylmethylcellulose phthalate, hydroxypropylmethylcellulose acetate succinate, carboxymethylcellulose ether, polyvinylacetate phthalate, polyester of styrene and maleic acid copolymer, polyester of vinylether and maleic acid copolymer, vinylacetate and crotonic acid copolymer, copolymers of methacrylic acid and ethylacrylate, copolymers of methacrylic acid and methacrylate (e.g., EUDRAGIT® L100, EUDRAGIT® L100-55, EUDRAGIT® L 30 D-55, and EUDRAGIT® S100), ethylcellulose, copolymers of methacrylate/trimethylamonioethylmethacrylate (e.g., EUDRAGIT® RL PO, EUDRAGIT® RL 100, EUDRAGIT® RL 30D, EUDRAGIT® RS PO, EUDRAGIT® RS 100, and EUDRAGIT® RS 30D), neutral polymers of methacrylate (e.g., EUDRAGIT® NE 30 D and EUDRAGIT® NE 40 D) and mixtures thereof.

Specific examples of the combination include a combination of polymers which are insoluble in an aqueous medium with water-soluble polymers such as a combination of ethylcellulose or methacrylate/trimethylammonioethylmethacrylate copolymers (e.g., EUDRAGIT® RL PO, EUDRAGIT® RL 100, EUDRAGIT® RL 30 D, EUDRAGIT® RS PO, EUDRAGIT® RS 100, and EUDRAGIT® RS 30 D) or neutral methacrylate polymers (e.g., EUDRAGIT® NE 30 D and EUDRAGIT® NE 40D) with water-soluble polymers such as hydroxypropylmethylcellulose, hydroxypropylcellulose, hydroxyethylcellulose, methylcellulose and polyvinylpyrrolidone.

The thickness of the coating is critical for controlling the release of the active ingredient. The extended-release coating is applied until there is a weight gain of 3% to 15% w/w based on the total weight of the dosage form.

The term "osmotic agent", as used herein, includes all pharmaceutically acceptable inert water-soluble compounds. Examples of compounds suitable as osmotic agents include, but are not limited to, water-soluble salts of inorganic acids such as magnesium chloride or magnesium sulfate, lithium chloride, sodium chloride, potassium chloride, lithium hydrogen phosphate, sodium hydrogen phosphate, potassium hydrogen phosphate, lithium dihydrogen phosphate, sodium dihydrogen phosphate, and potassium dihydrogen phosphate; water-soluble salts of organic acids such as sodium acetate, potassium acetate, magnesium succinate, sodium benzoate, sodium citrate, and sodium ascorbate; non-ionic organic compounds with high water-solubility, e.g., carbohydrates such as mannitol, sorbitol, arabinose, ribose, xylose, glucose, fructose, mannose, galactose, sucrose, maltose, lactose, and raffinose; water-soluble amino acids such as glycine, leucine, alanine, or methionine; urea and urea derivatives; and mixtures thereof. The amount of osmotic agent used may vary from about 5% to about 20% w/w based on the total dosage form.

The semi-permeable layer of the present invention comprises one or more semi-permeable membrane-forming polymer(s), one or more flux enhancer(s), and one or more coating additive(s). A semi-permeable layer allows movement of water molecules through it, but does not allow contents of the shell to pass through.

Semi-permeable membrane-forming polymers are those which are not metabolized in the gastrointestinal tract, i.e., are ejected unchanged from the body in feces. Examples of semi-permeable membrane-forming polymers include, but are not limited to, cellulose derivatives such as cellulose acetate, ethyl cellulose, cellulose triacetate, agar acetate, amylose acetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate chloroacetate, cellulose acetate ethyl oxalate, cellulose acetate methyl sulphonate, cellulose acetate butyl sulphonate, cellulose acetate propionate, cellulose acetate diethylamino-acetate, cellulose acetate octate, cellulose acetate laurate, cellulose acetate p-toluenesulphonate, and cellulose acetate butyrate; polymeric epoxides; copolymers of alkylene oxides and alkyl glycidyl ethers; polyglycols or polylactic acid derivatives; copolymers of acrylic acid ethyl ester and methacrylic acid methyl ester; and mixtures thereof. Controlling semi-permeable membrane thickness also helps to control the permeability of the membrane, which generally may vary from about 3% to about 15% weight build up over the shell.

Flux enhancers are water-soluble substances which aid in drawing water from the surrounding media and are thereby helpful in manipulating the semi-permeable membrane's permeability. Specific examples of flux enhancers include, but are not limited to, hydroxymethyl cellulose, hydroxypropyl methylcellulose, polyethylene glycol, hydroxypropylcellulose, propylene glycol, polyvinylpyrrolidone, and mixtures thereof.

The immediate-release layer of the present invention comprises the active ingredient, one or more binder(s), one or more film forming polymer(s), and one or more coating additive(s).

Specific examples of binders include, but are not limited to, povidone, methyl cellulose, ethyl cellulose, hydroxypropyl cellulose, carboxymethyl cellulose, hydroxypropyl methyl cellulose, and mixtures thereof.

Specific examples of film-forming polymers include, but are not limited to, hydroxypropyl methylcellulose, hydroxypropylcellulose, ethylcellulose, methylcellulose, carboxymethyl cellulose, hydroxymethylcellulose, hydroxyethylcellulose, cellulose acetate, hydroxypropyl methylcellulose phthalate, cellulose acetate phthalate, cellulose acetate trimellitate; waxes such as polyethylene glycol; methacrylic acid polymers such as EUDRAGIT®; polyvinyl pyrrolidone; and mixtures thereof.

The term "pharmaceutically acceptable excipients" includes all the excipients used conventionally in the dosage forms, in particularly fillers.

Specific examples of fillers include, but not are limited to, talc, lactose, mannitol, colloidal silicon dioxide, stearic acid, magnesium stearate, calcium stearate, and mixtures thereof.

Coating additives may be selected from the group consisting of fillers, plasticizers, opacifiers, coloring agents, lubricants/glidants, and mixtures thereof.

Specific examples of plasticizers include, but are not limited to, triethylcitrate, dibutylsebacate, acetylated triacetin, tributylcitrate, glyceroltributyrate, diacetylated monoglyceride, rape oil, olive oil, sesame oil, acetyltributylcitrate, acetyltriethylcitrate, glycerin sorbitol, diethyloxalate, diethyl phthalate, diethylmalate, diethylfumarate, dibutylsuccinate, diethylmalonate, dioctylphthalate, and mixtures thereof.

Specific examples of opacifiers include, but are not limited to, titanium dioxide, manganese dioxide, iron oxide, silicon dioxide, and mixtures thereof.

Coating may be performed by applying the coating composition as a solution/suspension/blend using any conventional coating technique known in the prior art such as spray coating in a conventional coating pan or fluidized bed processor; dip coating; or compression coating.

Examples of solvents used for preparing the solution/dispersion of coating substances include methylene chloride, isopropyl alcohol, acetone, methanol, ethanol, water, and mixtures thereof.

The term "passageway", as used herein, covers any suitable means for releasing the active ingredient present in the shell into the surrounding media. The term includes passages, apertures, bores, holes, openings and the like, that are created through the semi-permeable layer and form a connection between the shell and the surrounding media. The passageway may be created by mechanical drilling or laser drilling, or be formed in response to the osmotic pressure acting on the drug delivery system. Based on the nature of the desired drug-release profile, the number and diameter of the passageways may be adjusted. However, the diameter of the passageway should not be large enough to allow body fluids to enter the drug delivery system by the process of convection.

The invention may be further illustrated by the following examples, which are for illustrative purposes only and should not be construed as limiting the scope of the invention in any way.

Examples 1-8

| Ingredients | Examples Amount (% w/w) | | | | | | | |
|---|---|---|---|---|---|---|---|---|
| | 1 | 2 | 3 | 4 | 5 | 6 | 7 | 8 |
| Core Composition | | | | | | | | |
| Pregabalin | 70.97 | 68.97 | 70.97 | 68.97 | 70.97 | 68.97 | 70.97 | 68.97 |
| Capsule Shell | 21.51 | 20.90 | 21.51 | 20.90 | 21.51 | 20.90 | 21.51 | 20.90 |
| Total Weight | 92.48 | 89.87 | 92.48 | 89.87 | 92.48 | 89.87 | 92.48 | 89.87 |
| Gelatin | 1.08 | 1.04 | 1.08 | 1.04 | 1.08 | 1.04 | 1.08 | 1.04 |
| Purified Water | q.s. | q.s. | q.s. | q.s. | q.s. | q.s. | q.s. | q.s. |
| Total Weight of Band Sealed Capsule | 93.56 | 90.91 | 93.56 | 90.91 | 93.56 | 90.91 | 93.56 | 90.91 |
| Coating Composition | | | | | | | | |
| Cellulose Acetate | 4.39 | 6.18 | 4.13 | 5.82 | 3.23 | 4.55 | 3.48 | 4.91 |
| Polyethylene Glycol (PEG 3350) | 0.65 | 0.91 | 1.29 | 1.82 | 1.29 | 1.82 | 1.29 | 1.82 |
| Polyethylene Glycol (PEG 400) | 0.65 | 0.91 | 0.65 | 0.91 | 1.16 | 1.64 | 1.29 | 1.82 |
| Triacetin | 0.77 | 1.09 | 0.39 | 0.55 | 0.77 | 1.09 | 0.39 | 0.55 |
| Acetone (95%) | q.s. | q.s. | q.s. | q.s. | q.s. | q.s. | q.s. | q.s. |
| Purified Water (5%) | q.s. | q.s. | q.s. | q.s. | q.s. | q.s. | q.s. | q.s. |
| Weight of Coating | 6.46 | 9.09 | 6.46 | 9.10 | 6.45 | 9.10 | 6.45 | 9.10 |
| Total Weight (Rounded Off) | 100.00 | 100.00 | 100.00 | 100.00 | 100.00 | 100.00 | 100.00 | 100.00 |

Process:

1. Pregabalin was filled into capsules and the capsules were locked.
2. A 10% w/w gelatin solution was prepared and the capsules were band sealed using it.
3. Acetone and purified water were mixed together.
4. Triacetin and Polyethylene Glycol 400 were added to the solution of step 3.
5. Polyethylene Glycol 3350 was dissolved in the solution of step 4 under continuous stirring.
6. Cellulose acetate was dissolved in the solution of step 5 under continuous stirring.
7. The coating solution of step 6 was used to coat the capsules of step 2 in a coating pan.

Example 9

| Ingredients | Amount (% w/w) |
|---|---|
| Trimetazidine Dihydrochloride | 27.27 |
| Capsule Shell | 45.45 |
| Total Weight | 72.72 |
| Gelatin | 2.27 |
| Purified Water | q.s. |
| Total Weight of Band Sealed Capsule | 74.99 |
| Semi-permeable Coat | |
| Cellulose Acetate | 7.95 |
| Polyethylene Glycol 3350 | 3.18 |
| Polyethylene Glycol 400 | 2.86 |
| Triacetin | 1.91 |
| Acetone (95%) | q.s. |
| Purified Water (5%) | q.s. |
| Weight of Coating | 15.90 |
| Total Weight | 90.89 |
| Drug Layering | |
| Trimetazidine Dihydrochloride | 4.55 |
| Hydroxypropylmethyl Cellulose | 4.55 |
| Ethanol (50%) | qs |
| Purified Water (50%) | qs |
| Total Weight (Rounded Off) | 100.00 |

Process:

1. Trimetazidine dihydrochloride was filled into capsules and the capsules were locked.
2. A 10% w/w gelatin solution was prepared and the capsules were band sealed using it.
3. Acetone and purified water were mixed together.
4. Triacetin and Polyethylene Glycol 400 were added to the solution of step 3.
5. Polyethylene Glycol 3350 was dissolved in the solution of step 4 under continuous stirring.
6. Cellulose acetate was dissolved in the solution of step 5 under continuous stirring.
7. The coating solution of step 6 was used to coat the capsules of step 2 in a coating pan.
8. Ethanol and purified water were mixed together.
9. Trimetazidine dihydrochloride was dissolved in the solution of step 8.

10. Hydroxypropylmethyl cellulose was dissolved in the solution of step 9 under continuous stirring. 11. The solution of step 10 was used to coat the capsules of step 7 in a coating pan.

Example 10

| Ingredients | Amount (% w/w) |
|---|---|
| Pregabalin | 55.56 |
| Mannitol | 17.78 |
| Talc | 0.74 |
| Capsule Shell | 18.52 |
| Weight | 92.60 |
| Gelatin | 0.93 |
| Purified water | q.s. |
| Total Weight of Band Sealed Capsule Coating | 93.53 |
| Ethylcellulose | 2.92 |
| Polyvinylpyrrolidone | 2.92 |
| Triethyl Citrate | 0.65 |
| Ethanol | q.s. |
| Weight of Coating | 6.49 |
| Total Weight (Rounded Off) | 100.00 |

Process:
1. Pregabalin, mannitol and talc were sifted and mixed together and then filled into capsules and the capsules were locked.
2. A 10% w/w gelatin solution was prepared and the capsules were band sealed using it.
3. Ethylcellulose was dissolved in ethanol under continuous stirring.
4. Triethyl citrate was added to the solution of step 3.
5. Polyvinylpyrrolidone (PVP K-30) was dissolved in the solution of step 4 under continuous stirring.
6. The coating solution of step 5 was used to coat the capsules of step 2 in a coating pan.

Example 11

| Ingredients | Amount (% w/w) |
|---|---|
| Pregabalin | 53.76 |
| Mannitol | 17.20 |
| Talc | 0.72 |
| Capsule Shell | 17.92 |
| Weight | 89.60 |
| Gelatin | 0.90 |
| Purified Water | q.s |
| Total Weight of Band Sealed Capsule Coating | 90.50 |
| EUDRAGIT ® RL PO | 5.38 |
| Triacetin | 0.54 |
| Talc | 3.58 |
| Ethanol | q.s. |
| Acetone | q.s. |
| Water | q.s. |
| Weight of Coating | 9.50 |
| Total Weight (Rounded Off) | 100.00 |

Process
1. Pregabalin, mannitol and talc were sifted and mixed together and then filled into capsules and the capsules were locked.
2. A 10% w/w gelatin solution was prepared and the capsules were band sealed using it.
3. Ethanol, acetone and water were mixed together.
4. Triacetin was added to the solution of step 3.
5. EUDRAGIT® RL PO was dissolved in the solution of step 4 under continuous stirring.
6. The coating solution of step 5 was used to coat the capsules of step 2 in a coating pan.

We claim:
1. A gastroretentive capsule dosage system consisting of:
(a) a shell filled with a powder consisting of an active ingredient, wherein the active ingredient is selected from the group consisting of acyclovir, gabapentin, pregabalin, trimetazidine, feropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifentidine, roxatidine, omeprazole, lansoprazole, pantoprazole, antacids selected from magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, furosemide, topiramide, hydrochlorothiazide, orlistat and pharmaceutically acceptable salts, esters or prodrugs thereof; and
(b) an extended-release coating over the shell, wherein the extended-release coating is applied in an amount of 3% to 15% w/w based on the total weight of the dosage system and comprises one or more extended release polymer(s) selected from group consisting of cellulose acetate, ethylcellulose and copolymers of methacrylate/trimethyl aminoethyl methacrylate, and the extended-release coating optionally comprises one or more coating additive(s), said additives being selected from the group consisting of fillers, plasticizers, opacifiers, coloring agents, lubricants/glidants and mixtures thereof.
2. A gastroretentive dosage system consisting of:
(a) a shell filled with a powder consisting of an active ingredient, wherein the active ingredient is selected from the group consisting of acyclovir, gabapentin, pregabalin, trimetazidine, feropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifenti- dine, roxatidine, omeprazole, lansoprazole, pantoprazole, antacids selected from magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, furosemide, topiramide, hydrochlorothiazide, orlistat and pharmaceutically acceptable salts, esters or prodrugs thereof;
- (b) an extended-release layer over the shell, wherein the extended-release layer is applied in an amount of 3% to 15% w/w based on the total weight of the dosage system and comprises one or more extended release polymer(s) selected from group consisting of cellulose acetate, ethylcellulose and copolymers of methacrylate/trimethyl aminoethyl methacrylate, and the extended-release layer optionally comprises one or more coating additive(s), said additives being selected from the group consisting of fillers, plasticizers, opacifiers, coloring agents, lubricants/glidants and mixtures thereof; and
- (c) an immediate-release layer comprising an active ingredient over the extended-release layer.

3. The gastroretentive dosage system of claim 2, wherein the active ingredient present in the shell and the active ingredient present in the immediate-release layer are the same or different.

4. A process for the preparation of a gastroretentive dosage system, wherein the process comprises the steps of:
- (a) filling an empty shell, wherein filling the empty shell consists of filling the empty shell with an active ingredient in powder form, wherein the active ingredient is selected from the group consisting of acyclovir, gabapentin, pregabalin, trimetazidine, feropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifentidine, roxatidine, omeprazole, lansoprazole, pantoprazole, antacids selected from magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, furosemide, topiramide, hydrochlorothiazide, orlistat and pharmaceutically acceptable salts, esters or prodrugs thereof; and
- (b) coating the shell consisting of the active ingredient with a solution or dispersion of one or more extended-release polymer(s) and one or more coating additive(s), wherein the extended-release polymer(s) is applied in an amount of 3% to 15% w/w based on the total weight of the dosage system and comprises one or more extended release polymer(s) selected from the group consisting of cellulose acetate, ethylcellulose and copolymers of methacrylate/trimethyl aminoethyl methacrylate, and the one or more coating additive(s) are selected from the group consisting of fillers, plasticizers, opacifiers, coloring agents, lubricants/glidants and mixtures thereof.

5. A process for the preparation of a gastroretentive dosage system, wherein the process comprises the steps of:
- (a) filling an empty shell, wherein filling the empty shell consists of filling the empty shell with an active ingredient in powder form, wherein the active ingredient is selected from the group consisting of acyclovir, gabapentin, pregabalin, trimetazidine, feropenem, carbidopa, levodopa, methyldopa, verapamil, propranolol, carvedilol, atenolol, albuterol, pirbuterol, nifedipine, nimodipine, nicardipine, amlodipine, prazosin, guanabenz, allopurinol, metoprolol, oxprenolol, baclofen, sumatriptan, benazepril, enalapril, lisinopril, captopril, quinapril, moxipril, indolapril, olindapril, retinapril, spirapril, cilazapril, perindopril, ramipril, zofenopril, fosinopril, nitrofurantoin, valacyclovir, azithromycin, inosine, didanosine, pranobex, tribavirin, vidarabine, simvastatin, pravastatin, atorvastatin, lovastatin, selegiline, midazolam, lithium carbonate, cimetidine, ranitidine, famotidine, nizatidine, bifentidine, nifentidine, roxatidine, omeprazole, lansoprazole, pantoprazole, antacids selected from magnesium carbonate, aluminum carbonate, aluminum hydroxide, magnesium oxide and sucralfate, carbenoloxalone, misoprostol, pirenzepine, telenzepine, bismuth salts, metronidazole, ciprofloxacin, clarithromycin, amoxicillin, cephalexin, ascorbic acid, folic acid, vitamin E, furosemide, topiramide, hydrochlorothiazide, orlistat and pharmaceutically acceptable salts, esters or prodrugs thereof;
- (b) coating the shell consisting of the active ingredient with a solution or dispersion of one or more extended-release polymer(s) and one or more optional coating additive(s), wherein the extended-release polymer(s) is applied in an amount of 3% to 15% w/w based on the total weight of the dosage system and comprises one or more extended release polymer(s) selected from the group consisting of cellulose acetate, ethylcellulose and copolymers of methacrylate/trimethyl aminoethyl methacrylate, and the one or more optional coating additive(s) are selected from the group consisting of fillers, plasticizers, opacifiers, coloring agents, lubricants/glidants and mixtures thereof; and
- (c) coating the above coated shells with a solution or dispersion of the active ingredient, one or more binder(s) and one or more coating additive(s).

6. The gastroretentive capsule dosage system of claim 1, wherein the extended-release coating further comprises one or more water soluble polymers selected from the group consisting of hydroxypropylmethylcellulose, hydroxypropylcellulose, hydroxyethyl cellulose, methylcellulose and polyvinylpyrrolidone.

* * * * *